United States Patent
Abedini et al.

(10) Patent No.: US 9,760,990 B2
(45) Date of Patent: Sep. 12, 2017

(54) CLOUD-BASED INFRASTRUCTURE FOR FEEDBACK-DRIVEN TRAINING AND IMAGE RECOGNITION

(71) Applicant: INTERNATIONAL BUSINESS MACHINES CORPORATION, Armonk, NY (US)

(72) Inventors: Mani Abedini, Melbourne (AU); Stefan Von Cavallar, Melbourne (AU); Rajib Chakravorty, Melbourne (AU); Matthew Aaron Davis, Prahran (AU); Rahil Garnavi, Macleod (AU)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 14/738,497

(22) Filed: Jun. 12, 2015

(65) Prior Publication Data
US 2016/0171682 A1    Jun. 16, 2016

Related U.S. Application Data

(60) Provisional application No. 62/091,554, filed on Dec. 14, 2014.

(51) Int. Cl.
*G06K 9/00* (2006.01)
*G06T 7/00* (2017.01)
(Continued)

(52) U.S. Cl.
CPC .......... *G06T 7/0012* (2013.01); *G06F 19/321* (2013.01); *G06F 19/345* (2013.01);
(Continued)

(58) Field of Classification Search
None
See application file for complete search history.

(56) References Cited

U.S. PATENT DOCUMENTS 8,873,836 B1*  10/2014  Dietrich .............. G06K 9/6267
                                                              382/155
2004/0122709 A1*  6/2004  Avinash ................ G06F 19/322
                                                              705/2

(Continued)

OTHER PUBLICATIONS

Dave et al "CloudClustering: Toward an iterative data processing pattern on the cloud", IEEE International Parallel & Distributed Processing Symposium, 2011.*

(Continued)

*Primary Examiner* — Shervin Nakhjavan
(74) *Attorney, Agent, or Firm* — F. Chau & Associates, LLC

(57) ABSTRACT

A method for a cloud-based feedback-driven image training and recognition includes receiving a set of expert annotations of a plurality of training images of a predetermined subject matter, wherein the expert annotations include a clinical diagnosis for each image or region of interest in an image, training one or more classification models from the set of expert annotations, testing the one or more classification models on a plurality of test images that are different from the training images, wherein each classification model yields a clinical diagnosis for each image and a confidence score for that diagnosis, and receiving expert classification result feedback regarding the clinical diagnosis for each image and a confidence score yielded by each classification model.

25 Claims, 5 Drawing Sheets

(51) Int. Cl.
   *G06F 19/00* (2011.01)
   *G06K 9/62* (2006.01)
(52) U.S. Cl.
   CPC ....... *G06K 9/00147* (2013.01); *G06K 9/6254* (2013.01); *G06K 9/6263* (2013.01); *G06K 2209/05* (2013.01); *G06K 2209/053* (2013.01); *G06T 2207/20081* (2013.01); *G06T 2207/20092* (2013.01); *G06T 2207/30048* (2013.01); *G06T 2207/30088* (2013.01)

(56) References Cited

U.S. PATENT DOCUMENTS

| | | | | |
|---|---|---|---|---|
| 2009/0198670 | A1* | 8/2009 | Shiffer | G06F 17/30675 |
| 2009/0305209 | A1* | 12/2009 | Graeber | G06F 19/363 434/262 |
| 2011/0301447 | A1* | 12/2011 | Park | G06T 7/0016 600/407 |
| 2012/0328178 | A1* | 12/2012 | Remiszewski | G06T 7/0028 382/133 |
| 2013/0191165 | A1* | 7/2013 | MacDonald | G06F 19/322 705/3 |
| 2014/0286561 | A1* | 9/2014 | Remiszewski | G06K 9/00127 382/133 |
| 2015/0086133 | A1* | 3/2015 | Grady | G06T 7/0022 382/278 |
| 2015/0106117 | A1* | 4/2015 | Ananda | G06F 19/345 705/3 |
| 2015/0213599 | A1* | 7/2015 | Buzaglo | G06T 7/0012 382/128 |

OTHER PUBLICATIONS

Hogan et al "NIST Cloud Computing Standards Roadmap", Computer Security Division Information Technology Laboratory National Institute of Standards and Technology Gaithersburg, MD 20899-8930 Jul. 2011.*

Lecznar et al "Cloud Computing Providers: Characteristics and Recommendations", G. Babin, K. Stanoevska-Slabeva, P. Kropf (Eds.): MCETECH 2011, LNBIP 78, pp. 32-45, 2011. Springer-Verlag Berlin Heidelberg 2011.*

* cited by examiner

DIAGNOSIS: MELANOMA

CLOUD-BASED INFRASTRUCTURE FOR FEEDBACK-DRIVEN TRAINING AND IMAGE RECOGNITION

CROSS REFERENCE TO RELATED UNITED STATES APPLICATIONS

This application claims priority from "A Cloud-Based Infrastructure for Feedback-Driven Training and Image Recognition", U.S. Provisional Application No. 62/091,554 of Abedini, et al., filed Dec. 14, 2014, the contents of which are herein incorporated by reference in their entirety.

TECHNICAL FIELD

This disclosure is directed to a scalable cloud infrastructure that implements new machine learning approaches to provide a feedback-driven training loop for image recognition.

DISCUSSION OF THE RELATED ART

Advanced techniques in machine learning combined with scalable "cloud" computing infrastructure are driving the creation of new and innovative health diagnostic applications. In addition, new and inexpensive computational and communication capabilities continue to drive growth in the amount of healthcare data generated. For example, the number of mammograms in the US has increased from 26 million in 2003 to over 48 million today, resulting annually in many petabytes of new image data alone. With the growth of other heterogeneous types of data, such as text, images, video, genetic sequences, etc., in a broad range of clinical domains, the need for new techniques and applications to store, process, and utilise this data continues to evolve.

Making sense of this large amount of data is a complex task. Algorithmic machine learning techniques can be used to extract useful information or model large data sets. In the context of clinical diagnosis, two classes of machine learning algorithms exist: Fully automated algorithms for diagnosis and algorithms that assist an expert clinician to perform the diagnosis, or computer assisted diagnosis (CAD). The purpose of computer-based systems is to support clinicians in their decision making, not to replace them. Therefore, CADs, rather than fully automated algorithms, have a better synergy in clinical environments by providing a suggestive diagnosis, or "second opinion", to assist a clinician and are already used in many routine clinical tasks.

Modern communication technologies permit remote access to computing resources, including processing, data storage, etc. This has significant benefits for clinical applications, making data collection, analysis, and reporting more flexible and reliable. The application of machine learning algorithms on a large amount of data requires massive computational infrastructure. Cloud computing provides a suitable model to access such computational systems in different levels—infrastructure, platform, software, and data. Despite some challenges, such as patient data privacy and associated regulatory concerns, cloud technologies are being adopted by organisations at an increasing rate. For health care providers, it presents a cost-effective way to get access to advanced technologies. Cloud computing platforms hide the complexity of multiple tools, operating platforms, and frameworks from the end user. Moreover, care providers in remote regions can obtain access to specialized resources, such as human experts, databases, digital models etc., in real time.

In the health care domain, machine learning algorithms require large volumes of training data to draw useful conclusions. Designing these algorithms to run efficiently on cloud-provided infrastructure is an effective strategy. Frameworks have been developed, such as MapReduce and GraphLab, which parallelize the execution of processing algorithms on the kinds of distributed infrastructure found in cloud environments. While these frameworks are more suitable for machine learning researchers than non-technical end-users, hosted software applications built on the same compute infrastructure and tailored for clinical users are becoming available.

SUMMARY

Exemplary embodiments of the disclosure as described herein generally include methods for performing training and recognition and scalable, cloud-based infrastructure systems for executing tasks against an analytics pipeline.

According to an embodiment of the disclosure, there is provided a method for a cloud-based feedback-driven image training and recognition, including receiving a set of expert annotations of a plurality of training images of a predetermined subject matter, wherein the expert annotations include a clinical diagnosis for each image or region of interest in an image, training one or more classification models from the set of expert annotations, testing the one or more classification models on a plurality of test images that are different from the training images, wherein each classification model yields a clinical diagnosis for each image and a confidence score for that diagnosis, and receiving expert classification result feedback regarding the clinical diagnosis for each image and a confidence score yielded by each classification model.

According to a further embodiment of the disclosure, the plurality of images are medical images, and the subject matter is a pre-selected portion of a patient's anatomy.

According to a further embodiment of the disclosure, an expert annotation further include a labeled image or region of interest in an image and a template with a feature associated with each label in the image or region of interest in an image.

According to a further embodiment of the disclosure, the feature is one of a low-level feature, a mid-level feature, or a high level feature. A low-level feature is directly extracted from image pixel data, a mid-level feature abstracts properties of the region of interest collected from the image annotations, and a high level feature is a domain specific property of a given image.

According to a further embodiment of the disclosure, training the one or more classification models includes creating a new training set of images by selecting one or more pre-annotated images that include images of mixed diagnoses, and training the one or more classification models on the new training set of images.

According to a further embodiment of the disclosure, training the one or more classification models further includes updating an existing classification model with addition expert annotations.

According to a further embodiment of the disclosure, the expert classification result feedback comprises a binary answer that indicates either agreement or disagreement with the clinical diagnosis and confidence score yielded by a classification model for an image.

According to a further embodiment of the disclosure, the expert classification result feedback further comprises a structured feedback option that receives answers to a series of questions presented after receipt of one or more binary answers.

According to a further embodiment of the disclosure, the expert classification result feedback comprises receiving a re-annotated classified image, wherein the classification model is retrained using the re-annotated classified image.

According to a further embodiment of the disclosure, the annotations include one or more of clinical diagnosis or histopathology of the image, a spatial boundary of a lesion, a number and types of colors observed in the lesion, identified patterns observed in the lesion According to a another embodiment of the disclosure, there is provided a system for cloud-based feedback-driven image training and recognition, including an image analytics pipeline configured to train and update one or more classification models from a set of expert annotations of a plurality of training images of a predetermined subject matter, and to use the one or more classification models to classify newly received images of the predetermined subject matter, an application middleware that provides a plurality of web services, a collection of worker processes for asynchronously executing tasks on the image analytics pipeline that are pooled, stateless execution routines that can be created and destroyed as needed, a priority job broker for queuing and distributing tasks from the application middleware to worker processes, and an extensible document and media storage platform configured to store results of the worker processes and the image analytics pipeline, where the system operates on public cloud service platforms, and supports a hybrid of public and private infrastructure.

According to a further embodiment of the disclosure, the plurality of consumable web services includes an application programming interface (API).

According to a further embodiment of the disclosure, the API uses a representational state transfer methodology and JavaScript Object Notation (JSON) data format.

According to a further embodiment of the disclosure, when a request is submitted, the requesting web service provides a task identifier, and the worker process handling the request either on-demand polls a result web service by providing the task identifier, or subscribes to an asynchronous messaging channel, wherein the requesting web service pushes the task identifier to the worker process handling the request when the worker process becomes available.

According to a further embodiment of the disclosure, when a worker process received a task from the job broker, the worker process downloads required models and data from a media store in the document and media storage platform, executes the analytic pipeline for a set of parameters, and returns an asynchronous response.

According to a further embodiment of the disclosure, the document and media storage platform includes a document store, multiple data stores, and distributed object stores.

According to a further embodiment of the disclosure, the image analytics pipeline includes an annotations template configured to receive expert annotations of an image, wherein the annotations include one or more of clinical diagnosis or histopathology of the image, a spatial boundary of a lesion, a number and types of colors observed in the lesion, identified patterns observed in the lesion.

According to a another embodiment of the disclosure, there is provided a non-transitory program storage device readable by a computer, tangibly embodying a program of instructions executed by the computer to perform the method steps for a cloud-based feedback-driven image training and recognition.

DETAILED DESCRIPTION OF EXEMPLARY EMBODIMENTS

Figure 1:
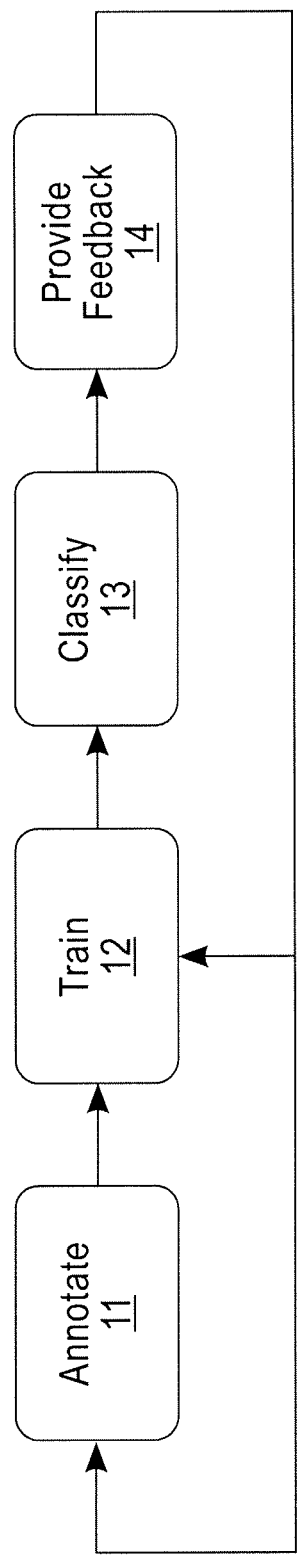
FIG. 1 depicts an analytics pipeline according to an embodiment of the disclosure.

Exemplary embodiments of the disclosure as described herein generally include methods for performing training and recognition and scalable, cloud-based infrastructure systems for executing tasks against an analytics pipeline. Accordingly, while the disclosure is susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications, equivalents, and alternatives falling within the spirit and scope of the disclosure.

As used herein, the term "image" refers to multi-dimensional data composed of discrete image elements (e.g., pixels for 2-dimensional images and voxels for 3-dimensional images). The image may be, for example, a medical image of a subject collected by computer tomography, magnetic resonance imaging, ultrasound, or any other medical imaging system known to one of skill in the art. The image may also be provided from non-medical contexts, such as, for example, remote sensing systems, electron microscopy, etc. Although an image can be thought of as a function from $R^3$ to R or $R^7$, the methods of the disclosure are not limited to such images, and can be applied to images of any dimension, e.g., a 2-dimensional picture or a 3-dimensional volume. For a 2- or 3-dimensional image, the domain of the image is typically a 2- or 3-dimensional rectangular array, wherein each pixel or voxel can be addressed with reference to a set of 2 or 3 mutually orthogonal axes. The terms "digital" and "digitized" as used herein will refer to images or volumes, as appropriate, in a digital or digitized format acquired via a digital acquisition system or via conversion from an analog image.

Exemplary embodiments of the disclosure can provide a new, feedback-driven application for performing image training and recognition, targeting dermoscopy image recognition and melanoma identification as exemplary, non-limiting applications. It is to be understood, however, that the dermoscopy image recognition and melanoma identification are for illustrative purposes, and embodiments of the disclosure can provide image training and recognition for any application that requires the use of images. An application according to embodiments of the disclosure can provide a web application and web service to clinical practices, potentially scaling to thousands of users, while hiding the complexities of a modern machine learning system from medical domain experts. A system according to embodiments of the disclosure implements new machine learning approaches to provide a feedback-driven training loop. This training sequence enhances classification performance by incrementally retraining the classifier model from expert responses. To easily provide an application according to embodiments of the disclosure and associated web service to clinical practices, a scalable cloud infrastructure is provided that is deployable in public cloud infrastructure and in private, on-premise systems.

A system according to embodiments of the disclosure includes two high-level components, a machine learning and analytics pipeline for performing training and recognition and a scalable, cloud-based infrastructure for storing models and media and for executing tasks against the analytics pipeline.

A supervised machine learning work flow according to an embodiment of the disclosure uses features or properties of images from various classes to build a model. These features are collected from the image by applying a number of image processing algorithms. The collected features can roughly be divided in three broad categories: Low, mid, and high-level features.

Low-level features are directly extracted from image pixel data. Histograms of pixel values or other empirical modelling of the pixel intensity distribution is one such low level feature.

Mid-level features try to abstract some properties of an object of interest, collected from an image annotation. Typically, operations or processes take place on raw pixel intensities that result in higher-level features. One such example is an "edge", roughly a gradient operation on raw pixel intensities. Horizontal, vertical or diagonal edges or any combination thereof can be easily obtained. Similarly, operators to detect corners, textures, and shapes are also available.

High-level features represent domain specific properties of a given image. For example, in a cardiac magnetic resonance (MR) image, an enlarged myocardium, or an infarct scar, can be a high-level feature.

Based on expert opinions, such as annotations from domain experts, features can be extracted either from an entire image, a partial image, or both, to capture local and/or global features from a single image.

According to an embodiment of the disclosure, a user can choose from a number of pre-defined features to be extracted from the image. The choice can be made available from a user interface or via a configuration file.

Machine Learning and Analytics Pipeline

FIG. 1 depicts an analytics pipeline according to an embodiment of the disclosure. As shown in FIG. 1, an analytics pipeline contains four subcomponents: an annotation stage 11, a training stage 12, a classification stage 13, and a feedback stage 14. Three of these stages are used in a traditional machine learning pipeline, namely, annotation, training, and classification. The pipeline also incorporates a fourth stage for providing feedback, which takes user feedback from a classification result to refine the classifier through incremental training.

Annotation Stage

For automated analysis and recognition of images of a certain class/type, annotation is prerequisite to training. In an annotation phase according to an embodiment of the disclosure, a domain expert generates ground truths and training samples for the training module. In other words, annotation is the process of attaching metadata to images to facilitate the development of classification models. In a computer-assisted system for melanoma recognition, for example, annotations can include:

clinical diagnosis or histopathology of the given image (i.e. melanoma vs. benign);
 spatial boundary of a lesion, separating the lesion from surrounding normal skin;
 number and types of colours, e.g. light brown, dark brown, black, etc., observed in the lesion; and
 identified dermoscopy patterns, such as a reticular pattern, globular pattern, pigment network, etc., observed in the lesion.

Clinical approaches, such as pattern analysis, the ABCDE rule of dermoscopy, the CASH (color, architecture, symmetry, and homogeneity) algorithm, etc., can be used as a basis for defining an "annotation template" to be applied by the domain expert, such as a clinician, in the annotation phase.

Figure 2:
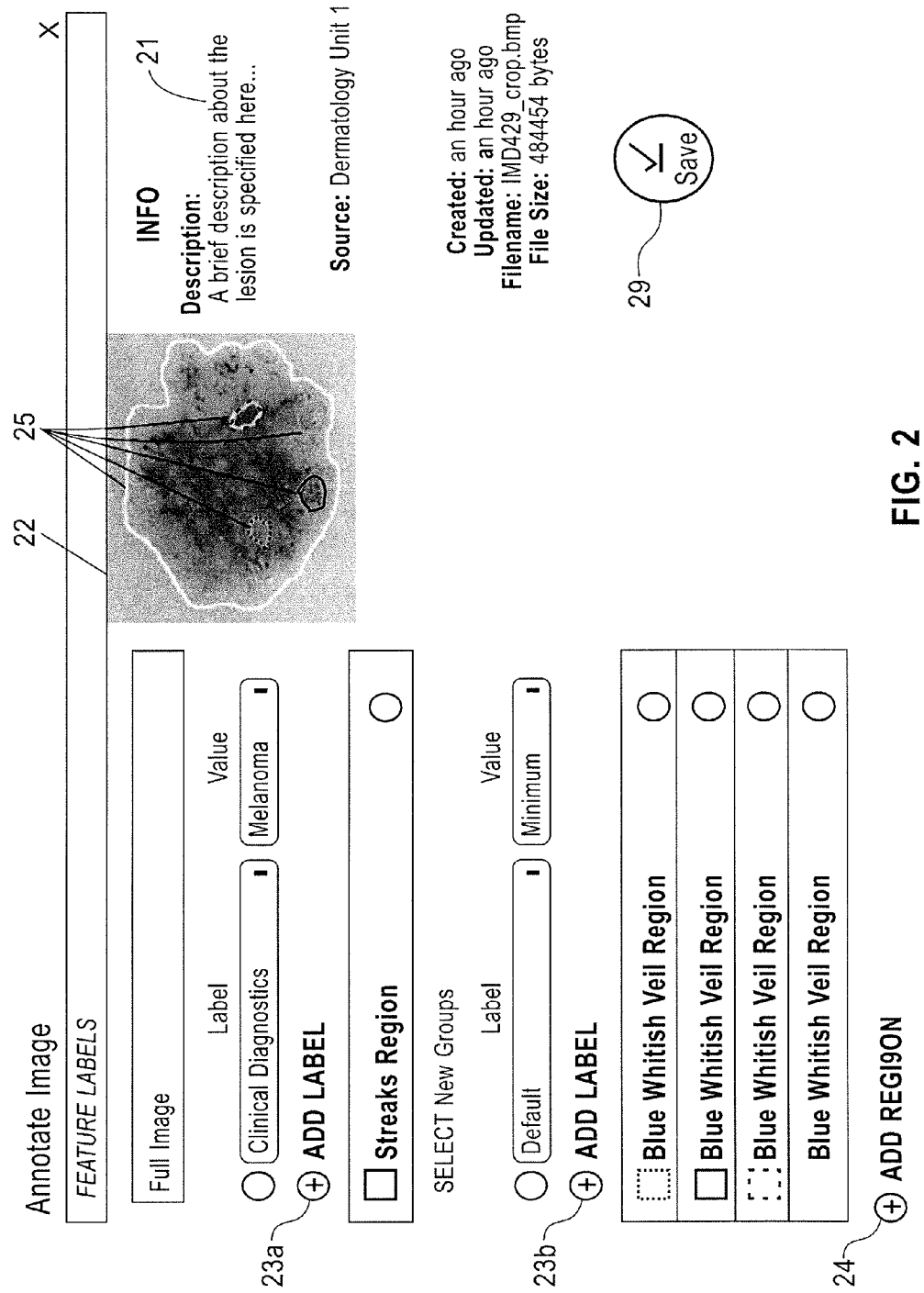
FIG. 2 depicts an image annotation tool according to an embodiment of the disclosure.

An embodiment of the disclosure provides an image annotation tool, as shown in FIG. 2, to simplify the process of defining annotations for an image. An exemplary, non-limiting image annotation tool as shown in FIG. 2 includes an image 22 of a region of interest, one or more regions of interest 25 defined by borders drawn by the clinician. The regions of interest may overlap each other, or some may be insider others. The image annotation tool may also include a place 21 to enter an overall description of the lesion, known as meta data. This information may optionally include clinical/diagnostic information. The image annotation tool may also include button 23a for adding labels for the entire image, including the diagnostic result, regardless of the specific region of interest, button 23b for adding labels for a specific region of interest 25, a button 24 for defining new sub-regions, and a button 29 for saving the annotations. The largest region of interest in FIG. 2 is the lesion border, which is in the list on the left side, and the remaining sub regions (ROIs) are independent of each other. However, since most of the important ROIs are located inside the mole or lesion, it is desirable to see such a pattern in the exemplar image. An annotation tool according to an embodiment of the disclosure can enable a clinician to identify features in an image from one or more templates provided through configuration. Labels can be applied to the full image or to spatial regions of interest, such as a lesion border. In addition to feature labelling, a clinician can also specify a clinical diagnosis for each image, such as melanoma or benign.

Training Stage

After attaching annotations to training samples in the annotation stage 11, a clinician or user can train and build a classification model in the training stage 12. First, the user creates a training dataset by selecting from one or more pre-annotated images. A training set will contain images of mixed diagnosis, such as images with benign lesions and those diagnosed as melanoma. After creating the training set, the user can launch a training algorithm by, for example, selecting "Train New Model" in a user interface. While a system according to an embodiment of the disclosure may default to a pre-configured set of parameters, experienced users can optionally fine-tune parameters provided to the training algorithms.

One feature of a system according to an embodiment of the disclosure can enable a domain expert to improve previously built models. After annotating new samples and adding them to a dataset for a previously trained model, a user can update the model. For example, a user can select "Update Model" in a user interface. This will trigger an incremental learning mechanism, which updates the existing classifier and builds an enhanced classification model without retraining with the entire training set.

Classification Stage

Figure 3:
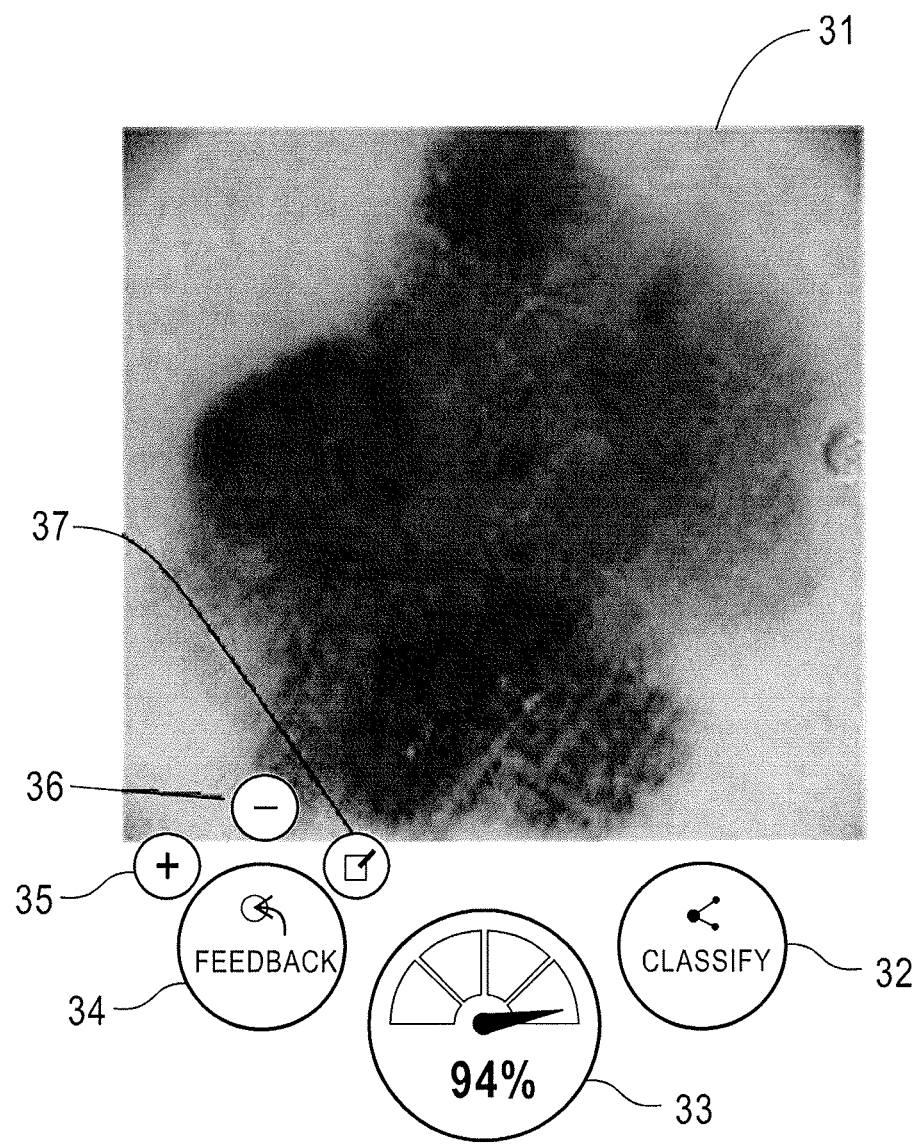
FIG. 3 depicts a popup window for providing feedback to a classifier according to an embodiment of the disclosure.

After building a model in the training stage 12, a clinician can now test the model on unseen images in a classification stage 13. Embodiments of the disclosure can enable a fast classification by uploading a dermoscopy image. Using one or more classification models developed in the training stage, the classification stage 13 can provide a diagnosis, such as melanoma vs. normal, and a confidence score on the classification results, as shown in FIG. 3. For example, FIG. 3 shows an image 31 to be classified with a button 32 to select "Classify", and a classification result 33 of melanoma with a 94% confidence.

Feedback Stage

To continually improve classifier performance, embodiments of the disclosure can provide a mechanism to gather classification result feedback from expert users. As shown in FIG. 3, after a classification is complete, a clinician can choose to provide feedback on the classifier score, by selecting the "Feedback" button 34. Feedback can be provided in two ways. The simplest way is a binary answer, either agree or disagree with the diagnosis or score, as indicated by the "+" and "−" buttons 35, 36 above the "Feedback" button 34. Embodiments of the disclosure may also provide a comprehensive feedback option. This second comprehensive feedback option enables the user to "mark up" the classified image by providing a new annotation, indicated by the button 37, which enables the clinician to enter written feedback. For example if the diagnosis is Melanoma, a sub category, such as superficial spreading melanoma, may be specified. In other embodiments, the feedback may take the form of a table that pairs properties, such as Diagnosis, Borders, Number of detected colors, Shape, etc., with values, such as Melanoma, irregular, four, asymmetric, etc. In this process, the image annotation tool, shown in FIG. 2, can also be used to refine the annotation structure, including a clinical diagnosis.

According to embodiments of the disclosure, the binary feedback can be extended by providing a structured feedback option that presents a series of questions to the user to elicit more information regarding the feedback. The series of questions can be presented in a question/answer format, or through the steps of a user interface wizard. A structured feedback option according to an embodiment of the disclosure is not as simple as the 'Yes/No' of the binary option and not as comprehensive as the comprehensive annotation interface, and may be invoked when user decisions need clarification.

These feedback results can be stored in a database and can be reviewed by an expert to help refine the classifier. According to embodiments of the disclosure, a previously unused image, along with the new annotation, is then appended to the classifier model's existing training dataset and the classifier is incrementally retrained. When feedback is available from an expert, techniques such as stochastic gradient descent can be used to enable the online learning mechanism.

Scalable, Cloud-Based Infrastructure

Figure 4:
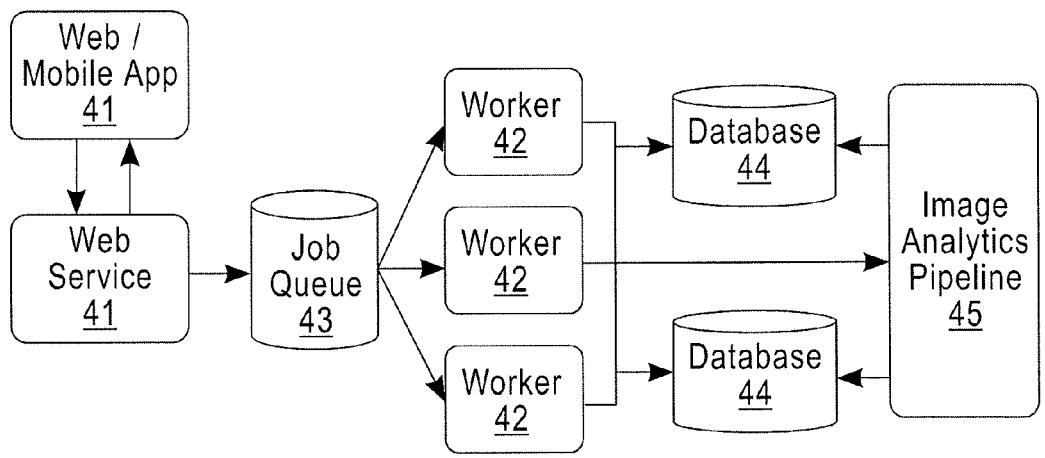
FIG. 4 depicts an overview of a system architecture according to an embodiment of the disclosure.

An infrastructure component according to an embodiment of the disclosure can be implemented using cloud-computing principals of elastic scaling and deployment platform flexibility. An exemplary, non-limiting overview of a system architecture according to an embodiment of the disclosure is shown in FIG. 4. The system architecture of FIG. 4 includes four subcomponents: an application middleware that provides consumable web services 41, a collection of worker processes for executing tasks on the analytics pipeline 42, a priority job broker for queuing and distributing tasks to workers 43, and an extensible document and media storage platform 44. The workers can execute jobs using the analytics pipeline 45. Each component shown in FIG. 4 can operate asynchronously and uses technologies, such as Web Sockets, to receive requests and provide an asynchronous response.

Web Services

A system according to an embodiment of the disclosure can be accessed through web service application programming interfaces (APIs). An exemplary, non-limiting API uses a representational state transfer (REST) methodology, JavaScript Object Notation (JSON) data format, and is implemented in JavaScript using Node.js, available at http://nodejs.org/. These APIs can provide an authenticated web service for submitting jobs for execution on the analytics pipeline 45. A system according to an embodiment of the disclosure can also provide a media management web service for uploading new media files for classification and training.

As many tasks are long-running, in that they take more than three seconds to complete, the web services 41 are designed to execute asynchronously. When a long-running request is submitted, the submitting web service 41 will provide an immediate synchronous response with a task identifier. The worker 42 handling the request has at least two options for receiving the acquiring response. First, the worker 42 can on-demand poll a result web service 41 by providing the task identifier. In addition, the worker 42 can subscribe to an asynchronous messaging channel using Web Sockets. In this situation, the web service 41 will push a response to the worker 42 as soon as it becomes available.

Computing and Storage Infrastructure

Execution of tasks on an analytics pipeline 45 according to an embodiment if the disclosure can be handled by a set of worker processes 42. An exemplary, non-limiting worker process 42 can be implemented in Python and can call machine learning runtimes using C, Java™, and Python code libraries. These workers provide an interface layer for accessing the analytics pipeline 45 in a scalable and predictable manner. Individual workers 42 can subscribe and listen for waiting tasks from a job broker 43. When a worker process 42 receives a job from the broker 43, it loads required models and data from a media store, executes the job in the analytic pipeline 45 for a set of parameters, either default or specified, and returns an asynchronous response. The worker processes 42 are pooled, stateless execution routines that can be created and destroyed as needed.

The job broker 43 monitors system load, and provisions or de-provisions virtual machine (VM) instances of worker processes 42 as needed. For each instance, a set of worker processes 42 can be spawned to fill available capacity, taking into account available CPU, memory, and network capacity. According to an embodiment of the disclosure, the job broker 43 can be implemented using Redis, available at http://redis.io/, to exclusively block and distribute waiting jobs, and Celery, available at http://www.celeryproject.org/, for managing distributed workers 42 on a set of VMs.

A system according to an embodiment of the disclosure can support several storage options. For metadata storage and management, a document store, such as MongoDB, available at http://www.mongodb.org/, can be used. For large, opaque binary data, including media (images) and classifier models, multiple data stores can be supported. In addition to a MongoDB-based storage backend, a system according to an embodiment of the disclosure can also support distributed object stores, such as Amazon Simple Storage Service (S3) (http://aws.amazon.com/) and OpenStack Swift (http://swift.openstack.org/).

While a system according to an embodiment of the disclosure can operate in public cloud service platforms, such as IBM BlueMix (https://console.ng.bluemix.net/) or Amazon Elastic Compute Cloud (EC2) (http://aws.amazon.com/), it can support a hybrid of public and private infrastructure. As many countries require personal health data to remain onshore, this separates web service APIs and applications from data storage and computation, which can simplify security and monitoring requirements. In addition, it may be inefficient or cost prohibitive to transfer and store certain types of media in cloud object or block stores. By keeping data on-site or providing a "bring your own" storage environment, data storage as well as billing and payment can be outsourced to other services or local infrastructure, further reducing security and latency concerns.

Results and Discussion

Annotating images for input into training modules is typically done using a spreadsheet tool such as Excel. In tests, the time to annotate a series of images using an image annotation tool according to an embodiment of the disclosure can be faster, especially for images that require drawn annotations.

Figure 5:
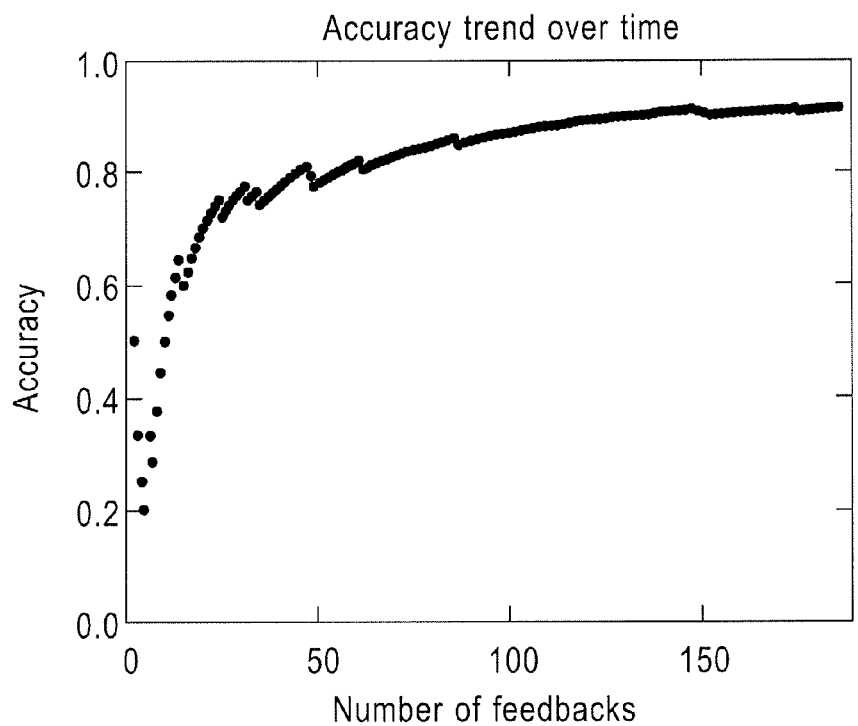
FIG. 5 illustrates an example of the accuracy of a classification model according to an embodiment of the disclosure.

A feedback mechanism according to an embodiment of the disclosure can enable incremental updates to the classification model as updates arrive over time. FIG. 5 illustrates an example of the accuracy of a classification model according to an embodiment of the disclosure as new user-provided feedback responses, either accepting or rejecting the prediction, are received over time. The example set contains both "agreement" and "disagreement" from the experts. The graph shows that a classifier according to an embodiment of the disclosure can struggle to correctly predict for the first few samples, but, as more feedback responses are received, the overall accuracy of the model improves. In this example, the classification accuracy for the first ten feedback responses is 56% but quickly improves to 75% over the next fifteen. The accuracy continues to improve with some fluctuation before converging at approximately 90% after 150 responses.

To test classifier performance and response time, a new classifier model according to an embodiment of the disclosure was built from a corpus of approximately 100 images. Five images of similar size and resolution were selected for classifier testing. Three images were of positive diagnosis (melanoma), two negative (normal skin). The five images were randomly selected and submitted in variable time increments to the web services 41, which submitted the images as jobs to the job broker 43. The job broker 43 and worker processes 42 were provisioned onto three virtual machines (VMs), each providing eight computing cores and 16 gigabytes of memory.

For each classification operation, a baseline response time was approximately 6.5 seconds per task with no additional system load, with an image upload time of 0.5-0.75 s and a classifier runtime of 5.7-6.0 s. As expected, by varying the number of concurrent worker processes 42 per VM, the classifier jobs were found to scale linearly with the number of computing cores, which indicates efficient CPU utilization by a classifier according to an embodiment of the disclosure. Increasing the number of concurrent jobs beyond the number of computing cores for the VM resulted in an increase of classification and queuing time.

System Implementations

As will be appreciated by one skilled in the art, embodiments of the present disclosure may be embodied as a system, method or computer program product. Accordingly, embodiments of the present disclosure may take the form of an entirely hardware embodiment, an entirely software embodiment, including firmware, resident software, microcode, etc., or an embodiment combining software and hardware embodiments that may all generally be referred to herein as a "circuit," "module" or "system." Furthermore, embodiments of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for embodiments of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Embodiments of the present disclosure are described below with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Figure 6:
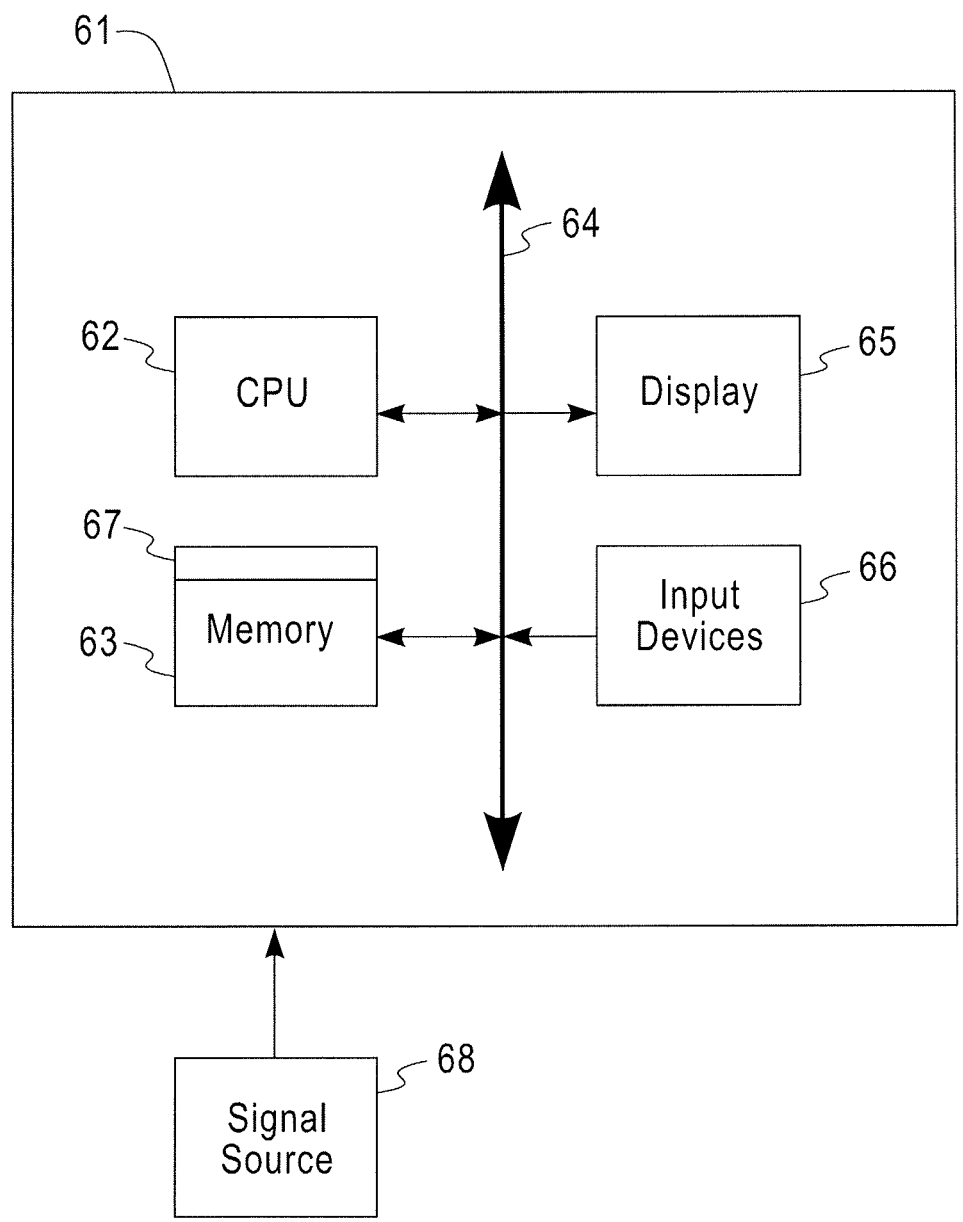
FIG. 6 is a block diagram of an exemplary computer system for a method for performing training and recognition and a scalable, cloud-based infrastructure for executing tasks against an analytics pipeline, according to an embodiment of the disclosure.

FIG. 6 is a block diagram of an exemplary computer system for implementing a method for a method for performing training and recognition and a scalable, cloud-based infrastructure for executing tasks against an analytics pipeline according to an embodiment of the disclosure. Referring now to FIG. 6, a computer system 61 for implementing the present disclosure can comprise, inter alia, a central processing unit (CPU) 62, a memory 63 and an input/output (I/O) interface 64. The computer system 61 is generally coupled through the I/O interface 64 to a display 65 and various input devices 66 such as a mouse and a keyboard. The support circuits can include circuits such as cache, power supplies, clock circuits, and a communication bus. The memory 63 can include random access memory (RAM), read only memory (ROM), disk drive, tape drive, etc., or a combinations thereof. The present disclosure can be implemented as a routine 67 that is stored in memory 63 and executed by the CPU 62 to process the signal from the signal source 68. As such, the computer system 61 is a general purpose computer system that becomes a specific purpose computer system when executing the routine 67 of the present disclosure.

The computer system 61 also includes an operating system and micro instruction code. The various processes and functions described herein can either be part of the micro instruction code or part of the application program (or combination thereof) which is executed via the operating system. In addition, various other peripheral devices can be connected to the computer platform such as an additional data storage device and a printing device.

The flowchart and block diagrams in the figures illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

While the present disclosure has been described in detail with reference to exemplary embodiments, those skilled in the art will appreciate that various modifications and substitutions can be made thereto without departing from the spirit and scope of the disclosure as set forth in the appended claims.

What is claimed is:

1. A method for a cloud-based feedback-driven image training and recognition, comprising the steps of:
   receiving a set of expert annotations of a plurality of training images of a predetermined subject matter, wherein the expert annotations include a clinical diagnosis for each image or region of interest in an image;
   training one or more classification models from the set of expert annotations;
   testing the one or more classification models on a plurality of test images that are different from the training images, wherein each classification model yields a clinical diagnosis for each image and a confidence score for that diagnosis; and
   receiving expert classification result feedback regarding the clinical diagnosis for each image and a confidence score yielded by each classification model,
   wherein the expert classification result feedback comprises receiving a re-annotated classified image, wherein the classification model is retrained using the re-annotated classified image, and
   wherein the steps of training one or more classification models and testing the one or more classification models on a plurality of test images are performed on a public cloud service platform.

2. The method of claim 1, wherein the plurality of images are medical images, and the subject matter is a pre-selected portion of a patient's anatomy.

3. The method of claim 1, wherein an expert annotation further include a labeled image or region of interest in an image and a template with a feature associated with each label in the image or region of interest in an image.

4. The method of claim 3, wherein the feature is one of a low-level feature, a mid-level feature, or a high level feature,
   wherein a low-level feature is directly extracted from image pixel data,
   a mid-level feature abstracts properties of the region of interest collected from the image annotations, and
   a high level feature is a domain specific property of a given image.

5. The method of claim 1, wherein training the one or more classification models includes creating a new training set of images by selecting one or more pre-annotated images that include images of mixed diagnoses; and training the one or more classification models on the new training set of images.

6. The method of claim 5, wherein training the one or more classification models further includes updating an existing classification model with addition expert annotations.

7. The method of claim 1, wherein the expert classification result feedback comprises a binary answer that indicates either agreement or disagreement with the clinical diagnosis and confidence score yielded by a classification model for an image.

8. The method of claim 7, wherein the expert classification result feedback further comprises a structured feedback option that receives answers to a series of questions presented after receipt of one or more binary answers.

9. The method of claim 1, wherein the annotations include one or more of clinical diagnosis or histopathology of the image, a spatial boundary of a lesion, a number and types of colors observed in the lesion, identified patterns observed in the lesion.

10. A system for cloud-based feedback-driven image training and recognition, comprising:
an image analytics pipeline configured to train and update one or more classification models from a set of expert annotations of a plurality of training images of a predetermined subject matter, to use the one or more classification models to classify newly received images of the predetermined subject matter, and receive expert classification result feedback regarding the clinical diagnosis for each image and a confidence score yielded by each classification model, wherein the expert classification result feedback comprises receiving a re-annotated classified image, wherein the classification model is retrained using the re-annotated classified image;
an application middleware that provides a plurality of web services;
a collection of worker processes for asynchronously executing tasks on the image analytics pipeline that are pooled, stateless execution routines that can be created and destroyed as needed;
a priority job broker for queuing and distributing tasks from the application middleware to worker processes; and
an extensible document and media storage platform configured to store results of the worker processes and the image analytics pipeline,
wherein the system operates on public cloud service platforms, and supports a hybrid of public and private infrastructure.

11. The system of claim 10, wherein the plurality of consumable web services includes an application programming interface (API).

12. The system of claim 11, wherein the API uses a representational state transfer methodology and JavaScript Object Notation (JSON) data format.

13. The system of claim 10, wherein when a request is submitted, the requesting web service provides a task identifier, and the worker process handling the request either on-demand polls a result web service by providing the task identifier, or subscribes to an asynchronous messaging channel, wherein the requesting web service pushes the task identifier to the worker process handling the request when the worker process becomes available.

14. The system of claim 10, wherein when a worker process received a task from the job broker, the worker process downloads required models and data from a media store in the document and media storage platform, executes the analytic pipeline for a set of parameters, and returns an asynchronous response.

15. The system of claim 10, wherein the document and media storage platform includes a document store, multiple data stores, and distributed object stores.

16. The system of claim 10, wherein the image analytics pipeline includes an annotations template configured to receive expert annotations of an image, wherein the annotations include one or more of clinical diagnosis or histopathology of the image, a spatial boundary of a lesion, a number and types of colors observed in the lesion, identified patterns observed in the lesion.

17. A non-transitory program storage device readable by a computer, tangibly embodying a program of instructions executed by the computer to perform the method steps for a cloud-based feedback-driven image training and recognition, the method comprising the steps of:
receiving a set of expert annotations of a plurality of training images of a predetermined subject matter, wherein the expert annotations include a clinical diagnosis for each image or region of interest in an image;
training one or more classification models from the set of expert annotations;
testing the one or more classification models on a plurality of test images that are different from the training images, wherein each classification model yields a clinical diagnosis for each image and a confidence score for that diagnosis; and
receiving expert classification result feedback regarding the clinical diagnosis for each image and a confidence score yielded by each classification model,
wherein the expert classification result feedback comprises receiving a re-annotated classified image, wherein the classification model is retrained using the re-annotated classified image, and
wherein the steps of training one or more classification models and testing the one or more classification models on a plurality of test images are performed on a public cloud service platform.

18. The computer readable program storage device of claim 17, wherein the plurality of images are medical images, and the subject matter is a pre-selected portion of a patient's anatomy.

19. The computer readable program storage device of claim 17, wherein an expert annotation further include a labeled image or region of interest in an image and a template with a feature associated with each label in the image or region of interest in an image.

20. The computer readable program storage device of claim 19, wherein the feature is one of a low-level feature, a mid-level feature, or a high level feature,
wherein a low-level feature is directly extracted from image pixel data,
a mid-level feature abstracts properties of the region of interest collected from the image annotations, and
a high level feature is a domain specific property of a given image.

21. The computer readable program storage device of claim 17, wherein training the one or more classification models includes creating a new training set of images by selecting one or more pre-annotated images that include images of mixed diagnoses; and
training the one or more classification models on the new training set of images.

22. The computer readable program storage device of claim 21, wherein training the one or more classification models further includes updating an existing classification model with addition expert annotations.

23. The computer readable program storage device of claim 17, wherein the expert classification result feedback comprises a binary answer that indicates either agreement or disagreement with the clinical diagnosis and confidence score yielded by a classification model for an image.

24. The computer readable program storage device of claim 23, wherein the expert classification result feedback further comprises a structured feedback option that receives answers to a series of questions presented after receipt of one or more binary answers.

25. The computer readable program storage device of claim 17, wherein the annotations include one or more of clinical diagnosis or histopathology of the image, a spatial boundary of a lesion, a number and types of colors observed in the lesion, identified patterns observed in the lesion.

* * * * *